US010287245B2

(12) United States Patent
Oehrlein et al.

(10) Patent No.: US 10,287,245 B2
(45) Date of Patent: May 14, 2019

(54) LIQUID THIOETHER CARBOXYLIC ACID ESTERS

(71) Applicant: BASF SE, Ludwigshafen (DE)

(72) Inventors: Reinhold Oehrlein, Rheinfelden-Herten (DE); Philip Caspari, Zurich (CH); Kurt Dietliker, Allschwil (CH); Natalia Kukaleva, Zurich (CH); David Niederer, Kuttigen (CH)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 15/512,595

(22) PCT Filed: Sep. 24, 2015

(86) PCT No.: PCT/EP2015/071926
§ 371 (c)(1),
(2) Date: Mar. 20, 2017

(87) PCT Pub. No.: WO2016/046292
PCT Pub. Date: Mar. 31, 2016

(65) Prior Publication Data
US 2018/0127363 A1 May 10, 2018

(30) Foreign Application Priority Data

Sep. 25, 2014 (EP) ..................... 14186475

(51) Int. Cl.
C07C 323/52 (2006.01)
C07D 339/08 (2006.01)
C07B 41/12 (2006.01)
C07C 319/18 (2006.01)
C09D 7/63 (2018.01)
G02B 3/14 (2006.01)
G02B 5/22 (2006.01)

(52) U.S. Cl.
CPC ............ *C07C 323/52* (2013.01); *C07B 41/12* (2013.01); *C07C 319/18* (2013.01); *C07D 339/08* (2013.01); *C09D 7/63* (2018.01); *G02B 3/14* (2013.01); *G02B 5/223* (2013.01)

(58) Field of Classification Search
CPC ..... C07B 41/12; C07C 319/18; C07C 323/52; C07D 339/08; G02B 3/14; G02B 5/223; C09D 7/63
See application file for complete search history.

(56) References Cited

U.S. PATENT DOCUMENTS 2,393,327 A * 1/1946 Langkammerer ..... C07C 323/00
  204/157.78
2,530,872 A * 11/1950 Gregory ................ C08K 5/372
  524/109

2,640,848 A   6/1953  Harman et al.
3,699,152 A * 10/1972  Hechenbleikner .... A23L 3/3463
  252/404
2014/0171597 A1  6/2014  Ma et al.

FOREIGN PATENT DOCUMENTS

DE  40 11 868 A1  10/1991
EP  0 284 374 A2  9/1988
EP  0 976 728 A1  2/2000
GB  1603651  *  4/1970
GB  1 603 651 A  11/1981
JP  48-5780 A  2/1973

OTHER PUBLICATIONS

Fehling et al. (Linear Copolymeric Poly(Thia-Alkanedioates) by Lipase-Catalyzed Esterification and Transesterification of 3,3(-Thiodipropionic Acid and Its Dimethyl Ester With α,ω-Alkanediols, Biotechnology and Bioengineering, 99, 5, pp. 1074-1084, Published Oct. 2007) (Year: 2007).*
Osvath et al. (Synthesis of a Large Cavity Homoleptic Thioether Cage and its Cobalt(III) Complex, J. Chem. Soc., Chem., Commun., pp. 40-42, published 1993) (Year: 1993).*
Ogata et al. (Active Polycondensation of Dicarboxylic acid Derivatives Having Beta-Hetero Atoms, Poly. J. 5, 2, pp. 186-194, Published 1973) (Year: 1973).*
International Search Report dated Jan. 19, 2016 in PCT/EP2015/071926 filed Sep. 24, 2015.
International Preliminary Report on Patentability and Written Opinion of the International Searching Authority dated Mar. 28, 2017 in PCT/EP2015/071926 filed Sep. 24, 2015.
Naoya Ogata, et al., "Active Polycondensation of Discarboxylic Acid Derivatives Having β-Hetero Atoms " Polymer Jounal, vol. 5, No. 2, XP055174091, Jan. 1, 1973, pp. 186-194.
Roberto Solaro, t al., "An Investigation of the Condensation Kinetics in Poly(Ester-Amide) and Poly(Ester-Sulphide) Preparation" Macromolecular Symposia, vol. 197, No. 1, XP055174080, Jul. 1, 2003, pp. 315-329.
Yasuo Suzuki, et al., "Synthesis and Characterization of High Refractive Index and High Abbe's Number Poly(Thioether Sulfone)s Based on Tricyclo [5.2.1.0$^{2,6}$] Decane Moiety" Macromolecules, vol. 45, No. 8, XP055172709, Apr. 24, 2012, pp. 3402-3408.

(Continued)

Primary Examiner — Yevgeny Valenrod
Assistant Examiner — Blaine G Doletski
(74) Attorney, Agent, or Firm — Oblon, McClelland, Maier & Neustadt, L.L.P.

(57) ABSTRACT

The present invention relates to a liquid thioether carboxylic acid ester, a process for the preparation of the liquid thioether carboxylic acid ester, an article comprising the liquid thioether carboxylic acid ester as well as a use of the liquid thioether carboxylic acid ester as a component or substantial part of an optical system, tunable lens, adaptive optical module and materials thereof, actuator, electro-active polymer, laser and all related products, optical liquid, cover glass, lens or container material, tiltable prism or optical calibration liquid or optical refractive index matching liquid and a use of the liquid thioether carboxylic acid ester as a component or substantial part of a color filter, window material, coating, varnish, lacquer, dye or pigment formulation, immersion liquid, ingredient or additive in a plastic material or ingredient or additive in a polymer.

10 Claims, No Drawings

(56) References Cited

OTHER PUBLICATIONS

Tsuyoshi Okubo, et al., "Synthesis, Characterization, and Optical Properties of Polymers Comprising 1,4-Dithiane-2,5-Bis (thiomethyl) Group" Journal of Applied Polymer Science, vol. 68, No. 11, XP055172715, Jun. 13, 1998, pp. 1791-1799.
Tsuyoshi Okubo, et al., "Preparation, Characterization, and Optical Properties of Disulfide-Comprising Oligo[2,5-Bis(Thiomethyl)-1,4-dDithiane] and its Poly[S-Alkylcarbamate]" Journal of Materials Science, vol. 34, 1999, pp. 337-347.
Office Action dated Jan. 14, 2019 in Chinese Patent Application No. 2015050800, filed Sep. 24, 2015 w/English translation.
Office Action dated Feb. 18, 2019, in European Patent Application No. 20150767491, filed Sep. 24, 2015.
T.Y Lee, et al., "Synthesis and Photopolymerization of Novel Multifunctional Vinyl Esters", Journal of Polymer Science, Part A: Polymer Chemistry, vol. 42, No. 17, Jul. 29, 2004, pp. 4424-4436, XP055554750.

* cited by examiner

LIQUID THIOETHER CARBOXYLIC ACID ESTERS

FIELD OF THE INVENTION

The present invention relates to a liquid thioether carboxylic acid esters, a process for the preparation of the liquid thioether carboxylic acid esters, an article comprising the liquid thioether carboxylic acid ester as an ingredient in at least one of its parts or as part of the article itself as well as a use of the liquid thioether carboxylic acid ester as a component or substantial part of an optical system, tuneable lens, adaptive optical module and materials thereof, actuator, electro-active polymer, laser and all related products, optical liquid, cover glass, lens or container material, tiltable prism or optical calibration liquid or optical refractive index matching liquid and a use of the liquid thioether carboxylic acid ester as a component or substantial part of a color filter, window material, coating, varnish, lacquer, dye or pigment formulation, immersion liquid, ingredient or additive in a plastic material or ingredient or additive in a polymer.

BACKGROUND OF THE INVENTION

The current development towards ever smaller and lighter optical systems demands novel approaches for the technical realization of optical devices for these intended applications. Especially heavy and slow optical devices based on glass and/or solid lens systems which are moved back and forward for focusing or zooming are sought to be replaced by so called liquid tuneable lens systems. The main part of such lens systems is a liquid-filled core element comprising a rigid container and a deformable membrane, which encloses a so-called "optical liquid". The lens is typically formed by a lens shaper, which defines the optically clear aperture of the lens and the initial deformation of the lens. In case of manually tuneable lenses (ML), the shaper is pushed directly into the membrane by hand/manually, whereas in case of electrically tuneable lenses (EL), an electromagnetically actuated bobbin is pushed into the membrane, deforming the liquid filled volume and therefore changing the curvature of the lens as a function of the applied force to the actuated bobbin.

The optical liquid is enclosed by a soft membrane and a rigid container. The initial shape of the lens is defined by the lens shaper and the amount of optical liquid in the volume. When a bobbin is pushed into the deformable membrane, fluid is pumped from the surrounding of the lens into the centre, resulting in a deformation of the central part of the lens and therefore in a change of the focal length of the lens.

The optical liquid is a crucial component of the liquid tuneable lens system. In particular, it is desirable that the optical liquids have high refractive index (1.5), Abbe's number ≥40, transparency in the visible range (400-800 nm) of at least 90%, low volatility, wide operational range of temperature from desirably about −20° C. to +100° C. and chemical compatibility with other components of the lens system (e. g. membranes, container materials, glues). Further, the viscosity of the optical liquids should be preferably not higher than 5000 mPas.

However, materials having high Abbe's numbers ν ($ν_d$=$(n_d-1)/(n_F-n_c)$ with refractive indices $n_d$ at 587.56 nm, $n_F$ at 486.1 nm, $n_c$ at 656.3 nm or $ν_D$=$(n_D-1)/(n_F-n_c)$ with refractive indices $n_D$ at 589.3 nm, $n_F$ at 486.1 nm, $n_c$ at 656.3 nm) as well as high refractive indices n (n=sin $α_i$/sin $α_r$), i meaning angle of incident light and r angle of reflective light) are not easy to obtain because said features normally cannot be enhanced in parallel. Thus, the materials presently available and which are used as optical liquids represent a compromise between those features.

In the art, several attempts for providing materials fulfilling at least some of these requirements have been proposed. For example, commercially available fluorocarbon/perfluoropolyether fluids (DuPont, Nye, Solvay Specialty Polymers) show Abbe's numbers of ν>100 but have refractive indices of n≈1.3. Recently, a new class of polythio ether sulfones based compounds exhibiting high Abbe's numbers and high refractive indices have been reported by Y. Suzuki et al. Macromolecules, 2012, 45, 3402. The polythio ether sulfones based compounds are of the following formula:

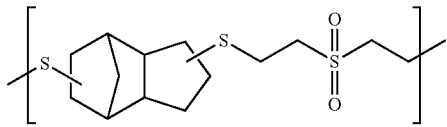

nD: 1.605 ; Abbe's Number 48.0

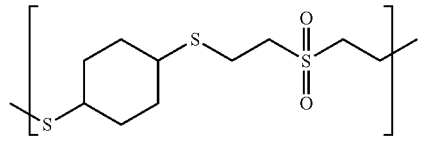

nD: 1.602 ; Abbe's Number 50.6

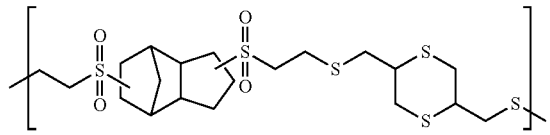

nD: 1.623 ; Abbe's Number 45.8

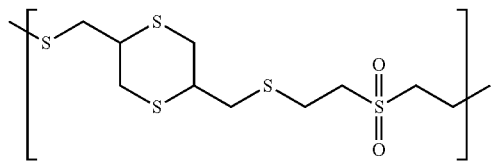

nD: 1.651 ; Abbe's Number 42.6

However, the afore-mentioned materials are solids at room temperature including their monomeric building blocks and are therefore not suitable as optical liquids in liquid tuneable lens systems.

Another class of materials has been disclosed by T. Okubo et al. J. Appl. Polmer Sci., 1998, 68, 1791 and T. Okubo et al. J. Mater Sci., 1999, 34, 337. Further, materials based on the thio phenol ether motif (n>1.6) are proposed as ingredients. The thio phenol ether motif of the materials is as follows:

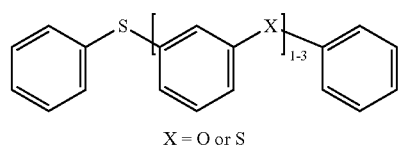

X = O or S

However, these compounds have Abbe's number of 23 and are only available as mixtures and are very costly. In addition the quality is variable and available amounts are low. Other materials containing an oligo-sulfide motif and additionally reactive acrylic residues are used to produce polymers with high $n_D$ and $v$ (see e.g. DE 4011868, EP 0 284 374 A2).

Thus, there is a need in the art for providing liquids which are suitable as optical liquids, especially in liquid tuneable lens systems. In particular, it is desirable to provide a liquid having high Abbe's number $v$ as well as high refractive index $n$. A high refractive index is needed for a high optical power whereas a high Abbe number is beneficial for low chromatic aberration/dispersion (dependency of the wave length on the refractive index).

Accordingly, it is an object of the present invention to provide a liquid which is suitable as optical liquid. Furthermore, it is an object of the present invention to provide a liquid which is suitable as optical liquid in liquid tuneable lens systems. It is an even further object of the present invention to provide a liquid having an improved balance of (high) Abbe's number $v$ and (high) refractive index $n$ (refractive index≈1.27 and higher, Abbe's number≈35 and higher). A still further object of the present invention is to provide a liquid having high transmittance in the visible range. An even further object of the present invention is to provide a liquid having good compatibility with the membrane materials. Further objects can be gathered from the following description of the invention.

SUMMARY OF THE INVENTION

The foregoing and other objects are solved by the subject-matter of the present invention. According to a first aspect of the present invention, a liquid thioether carboxylic acid ester is provided. The liquid thioether carboxylic acid ester is a reaction product of A) a compound of the formula
 a) (A1)

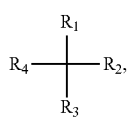
(A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by O, S and/or C=O; or b) (A2)

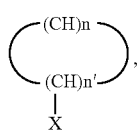
(A2)

wherein n' is 1 or 2, the sum of n and n' is an integer in the range from 5 to 9 and one or two $CH_2$-group(s) is/are replaced with S and/or O with the proviso that S and/or O are not directly linked, and X is $(CH_2)_m$—SH with m being an integer in the range from 0 to 3; or c) (A3)

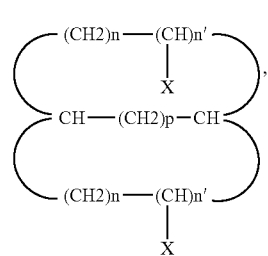
(A3)

wherein n' is 1 or 2, the sum of n and n' is an integer in the range from 5 to 9; X is $(CH_2)_m$—SH with m being an integer in the range from 0 to 3 and p is an integer in the range from 0 to 3; and B) a compound of the formula (B)

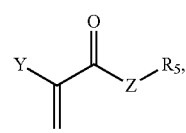
(B)

wherein Y is hydrogen or methyl; Z is O; $R_5$ is a linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl According to a further aspect of the present invention, a process for the preparation of a liquid thioether carboxylic acid ester, as defined herein, is provided. The process comprising the steps of A) providing a compound of the formula
 a) (A1)

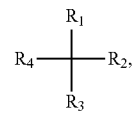
(A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by 0, S and/or C=; or b) (A2)

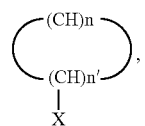
(A2)

wherein n' is 1 or 2, the sum of n and n' is an integer in the range from 5 to 9 and one or two $CH_2$-group(s) is/are replaced with S and/or O with the proviso that S and/or O are not directly linked, and X is $(CH_2)_m$—SH with m being an integer in the range from 0 to 3; or c) (A3)

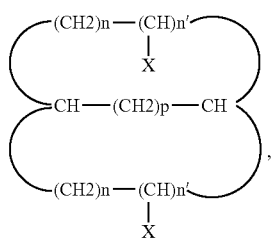

wherein n' is 1 or 2, the sum of n and n' is an integer in the range from 5 to 9; X is $(CH_2)_m$—SH with m being an integer in the range from 0 to 3 and p is an integer in the range from 0 to 3;

B) providing a compound of the formula (B)

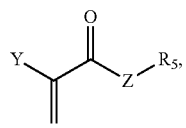

wherein Y is hydrogen or methyl; Z is O; $R_5$ is linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl, and C) reacting the compound of step A) with the compound of step B) such as to obtain the liquid thioether carboxylic acid ester.

According to an even further aspect of the present invention, an article, preferably an optical lens such as a tunable focus lens, optical liquid, tiltable prism or calibration liquid or refractive index matching liquid, comprising the liquid thioether carboxylic acid ester, as defined herein, as an ingredient in at least one of its parts or as part of the article itself is provided. According to another aspect of the present invention, an article, preferably an optical lens such as a tunable focus lens, optical liquid, tiltable prism or calibration liquid or refractive index matching liquid, comprising the liquid thioether carboxylic acid ester, as defined herein, as an ingredient in at least one of its parts or as a part of the article itself is provided.

According to a still further aspect, a use of the liquid thioether carboxylic acid ester, as defined herein, as a component or substantial part of an optical system, tunable lens, adaptive optical module and materials thereof, actuator, electro-active polymer, laser and all related products, optical liquid, cover glass, lens or container material, tiltable prism or optical calibration liquid or optical refractive index matching liquid is provided. According to still another aspect, a use of the liquid thioether carboxylic acid ester, as defined herein, as a component or substantial part of a color filter, window material, coating, varnish, lacquer, dye or pigment formulation, immersion liquid, ingredient or additive in a plastic material or ingredient or additive in a polymer is provided.

Advantageous embodiments of the inventive liquid thioether carboxylic acid ester are defined in the corresponding sub-claims.

According to one embodiment, in the formula (A1) $R_1$ is hydrogen or ethyl; $R_2$ is hydrogen or a linear $C_1$-$C_6$-alkyl containing at least one sulfhydryl moiety (SH); $R_3$ and $R_4$ are independently selected from a linear $C_2$-$C_6$-alkyl containing at least one sulfhydryl moiety (SH), and one or two $CH_2$ group(s) of $R_2$ and/or $R_3$ and/or $R_4$ is/are replaced by O, S and/or C=O.

According to another embodiment, in the formula (A1) $R_1$ is hydrogen; $R_2$ is a linear $C_1$-$C_5$-alkyl containing at least one sulfhydryl moiety (SH); $R_3$ and $R_4$ are independently selected from a linear $C_3$-$C_5$-alkyl containing at least one sulfhydryl moiety (SH), and one $CH_2$ group of $R_2$ and/or $R_3$ and $R_4$ is replaced by S.

According to yet another embodiment, in the formula (A1) $R_1$ is hydrogen or ethyl; $R_2$ is hydrogen or a linear $C_3$-$C_5$-alkyl containing at least one sulfhydryl moiety (SH); $R_3$ and $R_4$ are independently selected from a linear $C_3$-$C_5$-alkyl containing at least one sulfhydryl moiety (SH), and two $CH_2$ groups of $R_2$ and/or $R_3$ and $R_4$ are replaced by O and C=O.

According to one embodiment, two $CH_2$ groups of $R_2$ and/or $R_3$ and $R_4$ are replaced by O and C=O, and O and C=O are directly linked.

According to another embodiment, in the formula (A2) n' is 2; the sum of n and n' is an integer in the range from 5 to 7 and two $CH_2$-groups are replaced with S and/or O with the proviso that S and/or O are not directly linked, and X is $(CH_2)_m$—SH with m being an integer in the range from 1 to 3.

According to yet another embodiment, in the formula (A2) n' is 2; the sum of n and n' is 6; two $CH_2$-groups are replaced with S or O with the proviso that S or O are not directly linked, and X is $(CH_2)_m$—SH with m being 1.

According to one embodiment, Y is hydrogen or methyl; Z is O; $R_5$ is linear saturated $C_1$-$C_3$ alkyl.

According to another embodiment, Y is hydrogen or methyl; Z is O; $R_5$ is a linear or branched saturated $C_1$-$C_4$ alkyl or a saturated bicyclic aliphatic system selected from the group consisting of norbornyl-, isonorbornyl-, pinenyl-menthyl-, camphyl- or an aryl system selected from phenyl and benzyl.

According to yet another embodiment, the reaction product is obtained by a 1,4-addition mechanism of the at least one sulfhydryl group of the compound of the formula (A1), (A2) or (A3) and the compound of the formula (B).

According to one embodiment, the reaction product is of the general formula (C1), (C2) or (C3)

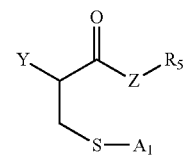

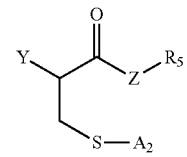

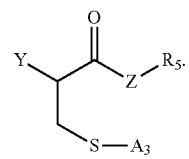

According to one embodiment, the thioether carboxylic acid ester has a refractive index of 1.27-1.9 and/or an Abbe's number of 35-110.

In the following, the details and preferred embodiments of the inventive liquid thioether carboxylic acid ester will be described in more detail. It is to be understood that these technical details and embodiments also apply to the inventive process for the preparation of a liquid thioether carboxylic acid ester, the inventive article comprising the liquid thioether carboxylic acid ester and its use.

DETAILED DESCRIPTION OF THE INVENTION

The thioether carboxylic acid ester of the present invention is a reaction product of A) a compound of the formula
  a) (A1)

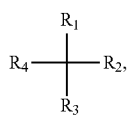

(A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by O, S and/or C=O; or b) (A2)

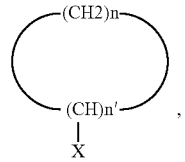

(A2)

wherein n' is 1 or 2, the sum of n and n' is an integer in the range from 5 to 9 and one or two $CH_2$- group(s) is/are replaced with S and/or O with the proviso that S and/or O are not directly linked, and X is $(CH_2)_m$—SH with m being an integer in the range from 0 to 3; or c) (A3)

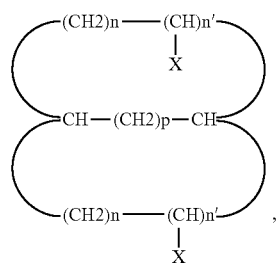

(A3)

wherein n' is 1 or 2, the sum of n and n' is an integer in the range from 5 to 9; X is $(CH_2)_m$SH with m being an integer in the range from 0 to 3 and p is an integer in the range from 0 to 3; and B) a compound of the formula (B)

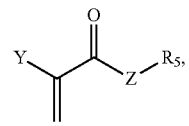

(B)

wherein Y is hydrogen or methyl; Z is O; $R_5$ is a linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl.

The term "at least one" sulfhydryl moiety (SH) means that the respective compound comprises one or more sulfhydryl moieties (SH).

In one embodiment, the at least one sulfhydryl moiety (SH) is one sulfhydryl moiety (SH). Alternatively, the at least one sulfhydryl moiety (SH) is two or more sulfhydryl moieties (SH). For example, the respective compound comprises two or three or four sulfhydryl moieties (SH). Preferably, the respective compound comprises two or three sulfhydryl moieties (SH).

In one embodiment, the compound of the formula (A1), (A2) or (A3), is the compound of the formula (A1)

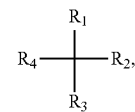

(A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by O, S and/or C=O.

In the formula (A1), $R_1$ is hydrogen, linear or branched $C_1$-$C_7$ alkyl, preferably $R_1$ is hydrogen, linear or branched $C_1$-$C_5$ alkyl, more preferably $R_1$ is hydrogen, linear or branched $C_1$-$C_4$ alkyl, even more preferably $R_1$ is hydrogen, linear or branched $C_2$-$C_4$ alkyl and most preferably $R_1$ is hydrogen or linear $C_2$-$C_3$ alkyl. For example, $R_1$ is hydrogen or ethyl. In one embodiment, $R_1$ is hydrogen.

Preferably, $R_1$ is unsubstituted linear or branched $C_1$-$C_7$ alkyl.

As used herein, the term "alkyl" is a radical of a saturated aliphatic group, including linear chain alkyl groups and branched chain alkyl groups.

In the formula (A1), $R_2$ is hydrogen or a linear or branched $C_1$-$C_8$-alkyl containing at least one sulfhydryl moiety (SH). Preferably, $R_2$ is hydrogen or a linear or branched $C_1$-$C_6$-alkyl containing at least one sulfhydryl moiety (SH), more preferably, $R_2$ is a linear or branched $C_1$-$C_5$-alkyl containing at least one sulfhydryl moiety (SH) and most preferably, $R_2$ is hydrogen or a linear or branched $C_3$-$C_5$-alkyl containing at least one sulfhydryl moiety (SH). For example, $R_2$ is a linear $C_1$-$C_5$-alkyl containing at least one sulfhydryl moiety (SH). Alternatively, $R_2$ is hydrogen or a linear $C_3$-$C_5$-alkyl containing at least one sulfhydryl moiety (SH).

In the formula (A1), $R_3$ and $R_4$ are independently selected from a linear or branched $C_1$-$C_8$-alkyl containing at least one sulfhydryl moiety (SH). Preferably, $R_3$ and $R_4$ are independently selected from a linear $C_2$-$C_6$-alkyl containing at least one sulfhydryl moiety (SH) and most preferably, $R_3$ and $R_4$ are independently selected from a linear $C_3$-$C_5$-alkyl containing at least one sulfhydryl moiety (SH).

In formula (A1), one or two $CH_2$ group(s) of $R_2$ and/or $R_3$ and/or $R_4$ can be replaced by O, S and/or C=O.

In one embodiment, one $CH_2$ group of $R_2$ and/or $R_3$ and $R_4$ is replaced by S. For example, one $CH_2$ group of $R_2$ or $R_3$ and $R_4$ is replaced by S. Alternatively, one $CH_2$ group of $R_2$ and $R_3$ and $R_4$ is replaced by S.

In another embodiment, two $CH_2$ groups of $R_2$ and/or $R_3$ and $R_4$ are replaced by O and C=O. For example, two $CH_2$ groups of $R_2$ or $R_3$ and $R_4$ are replaced by O and C=O. Alternatively, two $CH_2$ groups of $R_2$ and $R_3$ and $R_4$ are replaced by O and C=O. In one embodiment, two $CH_2$ groups of $R_2$ and/or $R_3$ and $R_4$ are replaced by O and C=O, wherein O and C=O are directly linked. For example, two $CH_2$ groups of $R_2$ or $R_3$ and $R_4$ are replaced by O and C=O, wherein O and C=O are directly linked. Alternatively, two $CH_2$ groups of $R_2$ and $R_3$ and $R_4$ are replaced by O and C=O, wherein O and C=O are directly linked.

Thus, it is preferred that in the formula (A1) $R_1$ is hydrogen or ethyl; $R_2$ is hydrogen or a linear $C_1$-$C_6$-alkyl containing at least one sulfhydryl moiety (SH); $R_3$ and $R_4$ are independently selected from a linear $C_2$-$C_6$-alkyl containing at least one sulfhydryl moiety (SH), and one or two $CH_2$ group(s) of $R_2$ and/or $R_3$ and/or $R_4$ is/are replaced by O, S and/or C=O.

More preferably, in the formula (A1) $R_1$ is hydrogen; $R_2$ is a linear $C_1$-$C_5$-alkyl containing at least one sulfhydryl moiety (SH); $R_3$ and $R_4$ are independently selected from a linear $C_3$-$C_5$-alkyl containing at least one sulfhydryl moiety (SH), and one $CH_2$ group of $R_2$ and/or $R_3$ and $R_4$ is replaced by S.

Alternatively, in the formula (A1) $R_1$ is hydrogen or ethyl; $R_2$ is hydrogen or a linear $C_3$-$C_5$-alkyl containing at least one sulfhydryl moiety (SH); $R_3$ and $R_4$ are independently selected from a linear $C_3$-$C_5$-alkyl containing at least one sulfhydryl moiety (SH), and two $CH_2$ groups of $R_2$ and/or $R_3$ and $R_4$ are replaced by O and C=O. In this embodiment, it is preferred that two $CH_2$ groups of $R_2$ and/or $R_3$ and $R_4$ are replaced by O and C=O, and O and C=O are directly linked.

It is appreciated that the compound of the formula (A1) is preferably selected from the group comprising, more preferably consisting of,

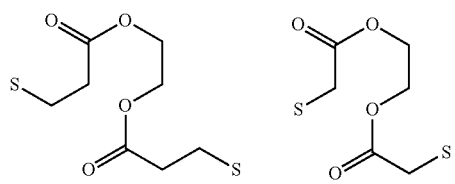

-continued

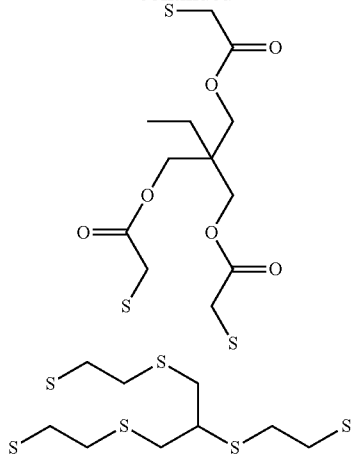

Alternatively, the compound of the formula (A1), (A2) or (A3), is the compound of the formula (A2)

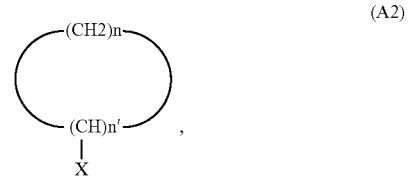

(A2)

wherein n' is 1 or 2, the sum of n and n' is an integer in the range from 5 to 9 and one or two $CH_2$-group(s) is/are replaced with S and/or O with the proviso that S and/or O are not directly linked, and X is $(CH_2)_m$—SH with m being an integer in the range from 0 to 3.

In the formula (A2), n' is 1 or 2, and preferably n' is 2.

In the formula (A2), n is preferably an integer in the range from 3 to 6, more preferably n is an integer in the range from 3 to 5, even more preferably, n is 4 or 5, and most preferably n is 4.

It is a further requirement in the formula (A2) that the sum of n and n' is an integer in the range from 5 to 9, preferably, the sum of n and n' is an integer in the range from 5 to 7 and most preferably, the sum of n and n' is 6.

Thus, it is appreciated that in the formula (A2) n' is 1 or 2 and the sum of n and n' is an integer in the range from 5 to 9. Preferably, n' is 1 or 2 and the sum of n and n' is an integer in the range from 5 to 7. More preferably, n' is 1 or 2 and the sum of n and n' is 5 or 6. Most preferably, n' is 2 and the sum of n and n' is 6.

In the formula (A2), one or two $CH_2$-group(s) is/are replaced with S and/or O with the proviso that S and/or O are not directly linked. Preferably, two $CH_2$-groups are replaced with S and/or O with the proviso that S and/or O are not directly linked. For example, two $CH_2$-groups are replaced with S and O with the proviso that S and O are not directly linked. Alternatively, two $CH_2$-groups are replaced with S or O with the proviso that S or O are not directly linked.

In one embodiment, two $CH_2$-groups in the formula (A2) are replaced with S with the proviso that the two S are not directly linked.

In the formula (A2), X is $(CH_2)_m$—SH with m being an integer in the range from 0 to 3. Preferably, X is $(CH_2)_m$SH with m being an integer in the range from 1 to 3. More preferably, X is $(CH_2)_m$—SH with m being 1 or 2. Most preferably, X is $(CH_2)_m$SH with m being 1.

Thus, it is preferred that in the formula (A2) n' is 2; the sum of n and n' is an integer in the range from 5 to 7 and two $CH_2$-groups are replaced with S and/or O with the proviso that S and/or O are not directly linked, and X is $(CH_2)_m$SH with m being an integer in the range from 1 to 3.

In one embodiment, n' is 2; the sum of n and n' is 6; two $CH_2$-groups are replaced with S or O with the proviso that S or O are not directly linked, and X is $(CH_2)_m$SH with m being 1 in the formula (A2).

It is appreciated that the compound of the formula (A2) is preferably

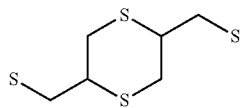

Alternatively, the compound of the formula (A1), (A2) or (A3), is the compound of the formula (A3)

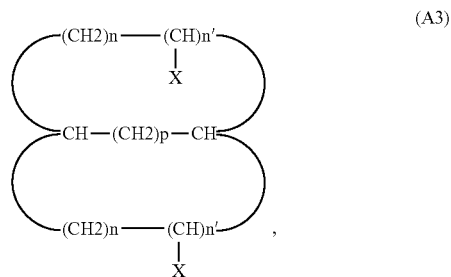

(A3)

wherein n' is 1 or 2, the sum of n and n' is an integer in the range from 5 to 9; X is $(CH_2)_m$SH with m being an integer in the range from 0 to 3 and p is an integer in the range from 0 to 3.

It is appreciated that the compound of the formula (A1), (A2) or (A3), is preferably a compound of the formula (A1) or (A2). In one embodiment, the compound of the formula (A1), (A2) or (A3), is a compound of the formula (A1). Alternatively, the compound of the formula (A1), (A2) or (A3), is a compound of the formula (A2). Preferably, the compound of the formula (A1), (A2) or (A3), is a compound of the formula (A1).

It is appreciated that the liquid thioether carboxylic acid ester of the present invention is a reaction product of the compound of the formula (A1), (A2) or (A3), and a compound of the formula (B)

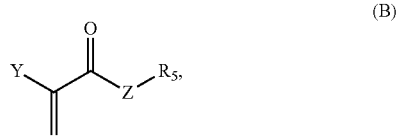

(B)

wherein Y is hydrogen or methyl; Z is O; $R_5$ is a linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl.

In the formula (B), Y is hydrogen or methyl. Preferably, Y is methyl. Alternatively, Y is hydrogen.

In the formula (B), $R_5$ is a linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl. For example, $R_5$ is a linear or branched saturated $C_1$-$C_8$ alkyl, preferably, $R_5$ is a linear or branched saturated $C_1$-$C_4$ alkyl and most preferably $R_5$ is a linear saturated $C_1$-$C_3$ alkyl. For example, $R_5$ is methyl or ethyl, such as methyl. Alternatively, $R_5$ is tert-butyl.

In one embodiment, $R_5$ is a saturated bicyclic aliphatic system selected from the group consisting of norbornyl-, isonorbornyl-, pinenyl-, menthyl-, camphyl- or an aryl system selected from phenyl and benzyl. Preferably, $R_5$ is an aryl system selected from phenyl and benzyl.

In one embodiment, Y is hydrogen or methyl; Z is O and $R_5$ is linear saturated $C_1$-$C_3$ alkyl in the formula (B). Preferably, Y is hydrogen or methyl; Z is O and $R_5$ is linear saturated $C_1$ or $C_2$ alkyl in the formula (B).

Alternatively, Y is hydrogen or methyl; Z is O; $R_5$ is a linear or branched saturated $C_1$-$C_4$ alkyl or a saturated bicyclic aliphatic system selected from the group consisting of norbornyl-, isonorbornyl-, pinenyl-menthyl-, camphyl- or an aryl system selected from phenyl and benzyl in the formula (B). Preferably, Y is hydrogen or methyl; Z is O; $R_5$ is a linear or branched saturated $C_2$-$C_4$ alkyl or a saturated bicyclic aliphatic system selected from the group consisting of norbornyl-, isonorbornyl-, pinenyl-menthyl-, camphyl- or an aryl system selected from phenyl and benzyl in the formula (B). More preferably, Y is hydrogen or methyl; Z is O; $R_5$ is a linear or branched saturated $C_3$ or $C_4$ alkyl, such as branched $C_4$ alkyl like tert-butyl, or a saturated bicyclic aliphatic system selected from the group consisting of norbornyl-, isonorbornyl-, pinenyl-menthyl-, camphyl- or an aryl system selected from phenyl and benzyl in the formula (B).

It is appreciated that the compound of the formula (B) is preferably selected from the group comprising, more preferably consisting of, methyl methacrylate, tert-butyl methacrylate, ethyl acrylate, benzyl methacrylate, iso-bornyl acrylate and mixtures thereof.

The compound of the formula (B) can be selected depending on the compound of the formula (A1), (A2) or (A3).

For example, if the liquid thioether carboxylic acid ester is a reaction product of the compound of the formula (A1) and the compound of the formula (B), the compound of the formula (B) is preferably selected such that Y is hydrogen or methyl; Z is O and $R_5$ is linear saturated $C_1$-$C_3$ alkyl, such as methyl.

Alternatively, if the liquid thioether carboxylic acid ester is a reaction product of the compound of the formula (A2) and the compound of the formula (B), the compound of the formula (B) is preferably selected such that Y is hydrogen or methyl; Z is O; $R_5$ is a linear or branched saturated $C_1$-$C_4$ alkyl or a saturated bicyclic aliphatic system selected from the group consisting of norbornyl-, isonorbornyl-, pinenyl-menthyl-, camphyl- or an aryl system selected from phenyl and benzyl.

It is appreciated that the liquid thioether carboxylic acid ester of the present invention is a reaction product of the compound of the formula (A1), (A2) or (A3), and a compound of the formula (B), wherein the reaction product is preferably obtained by a 1,4-addition mechanism of the at least one sulfhydryl group of the compound of the formula (A1), (A2) or (A3) and the compound of the formula (B). More preferably, the reaction product is obtained by a 1,4-Michael addition mechanism of the at least one sulfhydryl group of the compound of the formula (A1), (A2) or (A3) and the compound of the formula (B).

Accordingly, the liquid thioether carboxylic acid ester of the present invention is of the general formula (C1), (C2) or (C3)

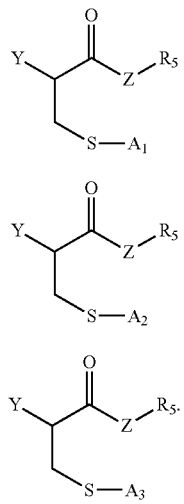

It is appreciated that the liquid thioether carboxylic acid ester of the general formula (C1), is a reaction product of the compound of the formula (A1) and the compound of the formula (B), wherein the residue A1 corresponds to the compound of the formula (A1) after its reaction with the compound of the formula (B).

The liquid thioether carboxylic acid ester of the general formula (C2) is a reaction product of the compound of the formula (A2) and the compound of the formula (B), wherein the residue A2 corresponds to the compound of the formula (A2) after its reaction with the compound of the formula (B).

The liquid thioether carboxylic acid ester of the general formula (C3) is a reaction product of the compound of the formula (A3) and the compound of the formula (B), wherein the residue A3 corresponds to the compound of the formula (A3) after its reaction with the compound of the formula (B).

As regards the definition of A1, A2, A3, Y, Z, $R_5$ and preferred embodiments thereof, reference is thus made to the statements provided above when discussing the technical details of the compounds of the formula (A1), (A2), (A3) and (B) of the present invention.

It is appreciated that the liquid thioether carboxylic acid ester of the present invention has specifically high Abbe's number u as well as high refractive index n.

For example, the thioether carboxylic acid ester has a refractive index of 1.27-1.9 and/or an Abbe's number of 35-110. Preferably, the thioether carboxylic acid ester has a refractive index of 1.27-1.9 or an Abbe's number of 35-110. Alternatively, the thioether carboxylic acid ester has a refractive index of 1.27-1.9 and an Abbe's number of 35-110. More preferably, the thioether carboxylic acid ester has a refractive index of 1.29-1.67 or an Abbe's number of 40-100. Alternatively, the thioether carboxylic acid ester has a refractive index of 1.29-1.67 and an Abbe's number of 40-100.

In one embodiment, the thioether carboxylic acid ester has a refractive index in the range of 1.45 and 1.67 and preferably in the range of 1.49 and 1.67.

Additionally or alternatively, the thioether carboxylic acid ester has an Abbe's number in the range of 35 to 100, preferably in the range of 38 to 100 and most preferably in the range of 40 to 100.

The present invention is further directed to a process for the preparation of the liquid thioether carboxylic acid ester.

The process comprising the steps of

A) providing a compound of the formula a) (A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by O, S and/or C=O; or b) (A2)

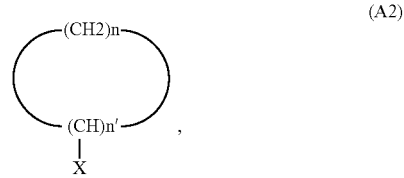

wherein n' is 1 or 2, the sum of n and n' is an integer in the range from 5 to 9 and one or two $CH_2$-group(s) is/are replaced with S and/or O with the proviso that S and/or O are not directly linked, and X is $(CH_2)_m SH$ with m being an integer in the range from 0 to 3; or c) (A3)

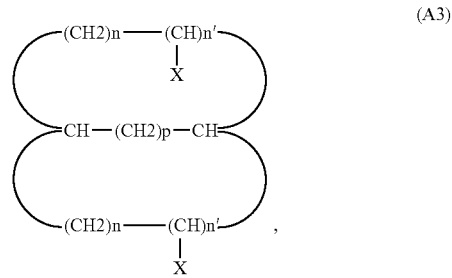

wherein n' is 1 or 2, the sum of n and n' is an integer in the range from 5 to 9; X is $(CH_2)_m SH$ with m being an integer in the range from 0 to 3 and p is an integer in the range from 0 to 3;

B) providing a compound of the formula (B)

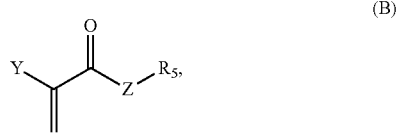

wherein Y is hydrogen or methyl; Z is O; $R_5$ is linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl, and C) reacting the compound of step A) with the compound of step B) such as to obtain the liquid thioether carboxylic acid ester.

As regards the definition of the compound of formula (A1), (A2), (A3), (B), the liquid thioether carboxylic acid ester and preferred embodiments thereof, reference is made to the statements provided above when discussing the technical details of the liquid thioether carboxylic acid ester of the present invention.

In one embodiment, process step C) is carried out such that the at least one sulfhydryl group of the compound of the formula (A1), (A2) or (A3) is reacted with the compound of the formula (B) by a 1,4-addition mechanism. Preferably, process step C) is carried out such that the at least one sulfhydryl group of the compound of the formula (A1), (A2) or (A3) is reacted with the compound of the formula (B) by a 1,4-Michael addition mechanism.

In one embodiment, process step C) is carried out in a suitable solvent. Preferably, process step C) is carried out in an organic solvent. The term "organic solvent" does not exclude that the organic solvent comprises minor amounts of water. If the organic solvent comprises water, the organic solvent comprises water in an amount of from 0.01 to 10.0 wt.-%, preferably from 0.01 to 5.0 wt.-%, more preferably from 0.01 to 2.0 wt.-% and most preferably from 0.01 to 1.0 wt.-%, based on the total weight of the solvent. For example, the organic solvent is free of water. In one embodiment, process step C) is carried out in a mixture of an organic solvent and water. If process step C) is carried out in a mixture of an organic solvent and water, the ratio of organic solvent to water (vol.-%/vol.-%) can be from 10:1 to 1:10, preferably from 5:1 to 1:5, even more preferably from 2:1 to 1:2 and most preferably about 1:1. In an alternative embodiment, process step C) is carried out in water.

Preferably, the solvent is selected such that the compound of the formula (A1), (A2) or (A3) as well as the compound of the formula (B) is soluble in the solvent, such as the organic solvent, mixture of organic solvent and water, or water.

The term "soluble" in the meaning of the present invention refers to systems in which no discrete solid particles of the compound of the formula (A1), (A2) or (A3) as well as the compound of the formula (B) are observed in the solvent, such as organic solvent, mixture of organic solvent and water, or water.

Preferably, the organic solvent is selected from the group comprising dimethylformamide, ethanol, tetrahydrofuran, dimethylformamide, methanol, toluene, xylene, ethyl acetate and mixtures thereof.

In one embodiment, the organic solvent comprises, preferably consists of, a mixture of organic solvents, preferably two or three organic solvents, and most preferably two organic solvents. For example, the organic solvent comprises, preferably consists of, a mixture of dimethylformamide and tetrahydrofuran. Alternatively, the organic solvent comprises, preferably consists of, a mixture of methanol and ethanol.

If the organic solvent comprises, preferably consists of, a mixture of two organic solvents, the organic solvents are preferably present in a ratio (vol:vol) ranging from 10:1 to 1:10, preferably from 5:1 to 1:5, even more preferably from 2:1 to 1:2 and most preferably about 1:1. For example, the organic solvent comprises, preferably consists of, a mixture of dimethylformamide and tetrahydrofuran in a ratio (vol:vol) ranging from 10:1 to 1:10, preferably from 5:1 to 1:5, even more preferably from 2:1 to 1:2 and most preferably about 1:1.

In one embodiment, process step C) is carried out in the presence of a catalyst. The catalyst is preferably a compound having a $pK_b$-value being suitable for deprotonating a sulfhydride, preferably for deprotonating the compound of formula (A1), (A2) or (A3) of process step A).

For example, the catalyst is selected from the group comprising alkali hydroxide, such as KOH, NaOH, $Mg(OH)_2$ or $Ca(OH)_2$; earth alkali hydroxide, such as $Na_2CO_3$, $K_2OC_3$ or $CaCO_3$; metal hydrogen carbonate, such as $NaHCO_3$, $KHCO_3$ or $Ca(HCO_3)_2$; metal alkoxide, tertiary amines, such as trialkyl amines, e.g. trimethyl amine, triethyl amine, tripropyl amine, tributyl amine, di-isopropyl ethyl amine, or aromatic amines, e.g. pyridine and mixtures thereof. Preferably, the catalyst is a tertiary amine, more preferably, the catalyst is a tertiary amine selected from the group comprising trimethyl amine, triethyl amine, tripropyl amine, tributyl amine, di-isopropyl ethyl amine and mixtures thereof and most preferably the catalyst is triethyl amine or di-isopropyl ethyl amine.

Additionally or alternatively, process step C) is carried out at a temperature ranging from −20° C. to the reflux temperature of the organic solvent, preferably of the organic solvent in which process step C) is carried out. In one embodiment, process step C) is carried out at a temperature ranging from 0° C. to the reflux temperature of the organic solvent, preferably of the organic solvent in which process step C) is carried out. For example, process step C) is carried out at a temperature ranging from room temperature to 40° C. Most preferably, process step C) is carried out at room temperature.

The term "room temperature" refers to a temperature typically measured in a laboratory, i.e. a temperature ranging from about 16 to 26° C., preferably from 18 to 25° C. and most preferably from 20 to 24° C.

The amounts of the compound of formula (A1), (A2) or (A3) and the compound of formula (B) in process step C) in order to reach the liquid thioether carboxylic acid ester can vary in a broad range and can be determined by appropriate calculation.

In one embodiment, the process for the preparation of the liquid thioether carboxylic acid ester further comprises a step D) of purifying the liquid thioether carboxylic acid ester obtained in step C).

It is appreciated that step D) of purifying the liquid thioether carboxylic acid ester obtained in step C) can be carried out by every means known to the skilled person for separating a compound from its reaction mixture. For example, process step D) can be carried out by methods selected from the group comprising, methods used for evaporating volatile compounds, such as in vacuum, extraction methods, distillation methods, chromatographic methods and mixtures thereof. Preferably, process step D) is carried out by evaporating volatile compounds, preferably in vacuum, extraction methods, distillation methods and chromatographic methods.

Thus, the process for the preparation of the liquid thioether carboxylic acid ester preferably comprises, more preferably consists of, the steps of A) providing a compound of the formula
  a) (A1)

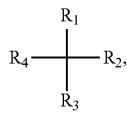

(A1)

wherein $R_1$ is hydrogen, linear or branched $C_1$-$C_7$ alkyl; $R_2$ is hydrogen or a linear or branched $C_1$-$C_8$-alkyl containing at least one sulfhydryl moiety (SH); $R_3$ and $R_4$ are independently selected from a linear or branched $C_1$-$C_8$-alkyl containing at least one sulfhydryl moiety (SH), and optionally one or two $CH_2$ group(s) of $R_2$ and/or $R_3$ and/or $R_4$ is/are replaced by O, S and/or C=O; or
  b) (A2)

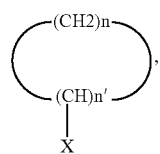

(A2)

wherein n' is 1 or 2, the sum of n and n' is an integer in the range from 5 to 9 and one or two $CH_2$-group(s) is/are replaced with S and/or O with the proviso that S and/or O are not directly linked, and X is $(CH_2)_m$SH with m being an integer in the range from 0 to 3; or
  c) (A3)

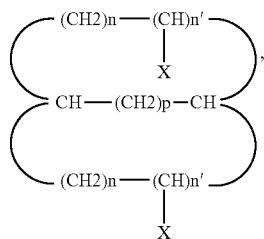

(A3)

wherein n' is 1 or 2, the sum of n and n' is an integer in the range from 5 to 9; X is $(CH_2)_m$SH with m being an integer in the range from 0 to 3 and p is an integer in the range from 0 to 3;

B) providing a compound of the formula (B)

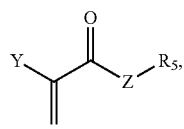

(B)

wherein Y is hydrogen or methyl; Z is O; $R_5$ is linear or branched saturated $C_1$-$C_8$ alkyl or a saturated bicyclic aliphatic system selected from the group consisting of norbornyl-, isonorbornyl-, pinenyl-, menthyl-, camphyl- or an aryl system selected from phenyl and benzyl;

C) reacting the compound of step A) with the compound of step B) such as to obtain the liquid thioether carboxylic acid ester; and D) purifying the liquid thioether carboxylic acid ester obtained in step C).

In one embodiment, the liquid thioether carboxylic acid ester is obtainable by the process for the preparation of a liquid thioether carboxylic acid ester as defined herein.

The instant invention is thus further directed to a liquid thioether carboxylic acid ester obtainable by the process for the preparation of a liquid thioether carboxylic acid ester of the instant invention.

With regard to the definition of the liquid thioether carboxylic acid ester and preferred embodiments thereof, reference is made to the statements provided above when discussing the technical details of the liquid thioether carboxylic acid ester of the present invention.

In view of the advantages obtained, the present invention is further directed to an article comprising the liquid thioether carboxylic acid ester as defined herein as an ingredient in at least one of its parts or as part of the article itself.

As regards the definition of the liquid thioether carboxylic acid ester and preferred embodiments thereof, reference is made to the statements provided above when discussing the technical details of the liquid thioether carboxylic acid ester of the present invention.

Preferably, the article comprising the liquid thioether carboxylic acid ester as an ingredient in at least one of its parts or as part of the article itself is an optical lens such as a tunable focus lens, optical liquid, tiltable prism or calibration liquid or refractive index matching liquid.

In one embodiment, the article comprising the liquid thioether carboxylic acid ester as an ingredient in at least one of its parts or as part of the article itself is an optical liquid.

In another embodiment, the article comprising the liquid thioether carboxylic acid ester as an ingredient in at least one of its parts or as part of the article itself is a wave guide material, color filter, window material, coating, varnish, lacquer, dye or pigment formulation, immersion liquid, ingredient or additive in a plastic material, ingredient or additive in a polymer.

Furthermore, the present invention is directed to a use of the liquid thioether carboxylic acid ester, as defined herein, as a component or substantial part of an optical system, tunable lens, adaptive optical module and materials thereof, actuator, electro-active polymer, laser and all related products, optical liquid, cover glass, lens or container material, tiltable prism or optical calibration liquid or optical refractive index matching liquid.

For example, the present invention is directed to a use of the liquid thioether carboxylic acid ester, as defined herein, as a component or substantial part of an optical liquid.

Further, the present invention is directed to a use of the liquid thioether carboxylic acid ester, as defined herein, as a component or substantial part of a color filter, window material, coating, varnish, lacquer, dye or pigment formulation, immersion liquid, ingredient or additive in a plastic material or ingredient or additive in a polymer.

With regard to the definition of the liquid thioether carboxylic acid ester and preferred embodiments thereof, reference is made to the statements provided above when discussing the technical details of the liquid thioether carboxylic acid ester of the present invention.

The scope and interest of the invention will be better understood based on the following examples which are intended to illustrate certain embodiments of the invention and are non-limitative.

EXAMPLES

1. Methods

NMR-Spectroscopy

NMR-data were acquired by using a Bruker Spectroscopin 300 at 300 K. The chemical shifts are given with respect to TMS as an internal standard δ-values (ppm). For the assignment of the signals and multiplicities the following abbreviations have been chosen: s—singulett, d—dublett, t—triplett, q—quartett, m—multiplett, b—broad, virt.—virtuell.

Refractive Index $n_D$ and Abbe's Nnumber $v_D$

Refractive index and Abbe's number were measured at 25° C. with the digital nine-wavelength (approximately 404.7, 435.8, 486.1, 546.1, 587.56, 589.3, 632.8, 656.3 and 706.5 nm) refractometer DSR-A of Schmidt & Haensch. The refractometer measures the critical angle of total reflection and calculates the refractive index from this value; the Abbe number ($v_D$) is calculated by the instrument automatically. For measurements, 300 μL of the corresponding liquid collected by Eppendorf Research® plus 100-1,000 μL pipette were used. The refractive index nis reported at 589.3 nm.

Gravity

Gravity has been defined as a mass of the 1 cm³ (1,000 μL) of liquid being collected by Eppendorf Research® plus 100-1,000 μL pipette and weighed using the Kern Electronic Analytical Balance Type ABS 120-4N with readability of 0.1 mg and reproducibility of 0.2 mg.

Viscosity

Dynamic shear viscosities of the synthesized liquids were measured in the cone-plate configuration with the Anton Paar MCR 301 rheometer operating in the rotational mode; the fixture CP50-0.5-SN20586 (diameter 50 mm and the angle of 0.5°) has been used as a measuring system; the gap size was set at 0.045 mm. Viscosities were measured as a continuous function of temperature (η–T)—within the temperature range from –20° C. to 100° C. The measurements were performed at two different shear rates: at 10 s$^{-1}$ and 100 s$^{-1}$.

2. Examples

Example 1 (A2 Series) BMSD-MA

Dimethyl-3'-(((1,4-dithiane-2,5-diyl)bis(methylene))bis(sulfanediyl))bis(2-methylpropanoate) BSMD-MA

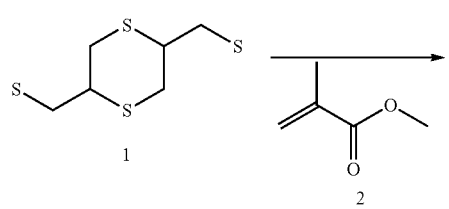

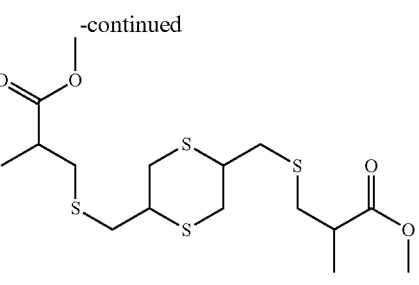

BMSD—MA

To 5 g (0.02 mol) BSMD 1 (T. Okubo et al. J. Appl. Poly Sci. 1998, 68, 1791) were added 7.5 g (0.07 mol) methyl methacrylate 2 in a mixture of 10 mL THF and 10 mL DMF. After addition of 1.4 mL (0.01 mol) triethyl amine the obtained solution was stirred for 72 h at room temperature. All volatile components were removed in vacuum, the residue was then treated with aqueous 1 N HCl, extracted with dichloromethane (DCM), dried over MgSO$_4$, filtered and evaporated. The residue was purified by column chromatography [c-hexane/ethyl acetate (5:1)] to give a colourless liquid (7.1 g, 73%).

NMR (400 MHZ, CDCl$_3$) δ=3.67 (s, 6H, OCH$_3$), 3.22-2.56 (m, 16H), 1.23-1.21 (d, 6H, CHCH$_3$).

$n_D$: 1.551; Abbe's numbers u: 43.76; sp. gravity: 1.968 g/ml; viscosity at 20° C.: 980 mPa s

Example 2 (A1 Series) GDMP-MA

Dimethyl 3,3'-(((ethane-1,2-diylbis(oxy))bis(3-oxopropane-3,1-diyl)) bis(sulfanediyl))bis(2-methylpropanoate) GDMP-MA

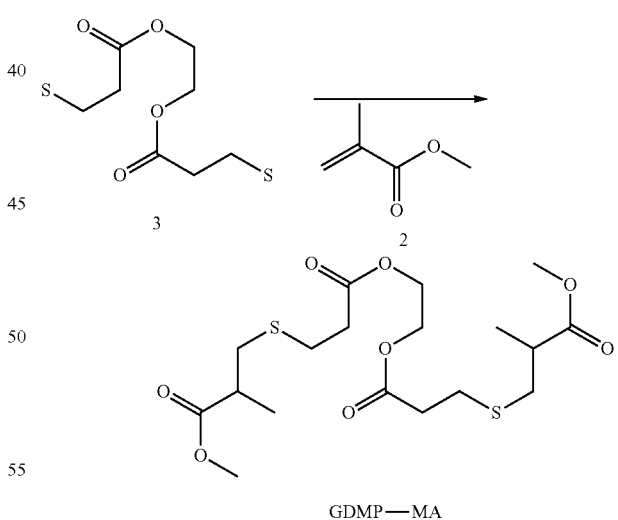

GDMP—MA 5 g (0.02 mol) of dithiol 3 were treated with 9.5 g (0.08 mol) methyl methacrylate 2 in a mixture of 10 mL THF and 10 mL DMA. 1.4 mL (0.01 mol) triethyl amine were added and the obtained solution was stirred for 72 h at room temperature. All volatile componentswere removed in vacuum, the residue was washed with aqueous 1 N HCl, extracted with dichloro methane, washed several times with water, dried over MgSO$_4$, filtered and evaporated to give a colourless liquid (7.1 g, 77%).

NMR (400 MHZ, CDCl$_3$) δ=4.26 (s, 4H, CH$_2$CO), 3.65 (s, 6H, OCH$_3$), 2.88-2.52 (m, 14H), 1.21-1.19 (d, 6H, CHCH$_3$).

n$_D$: 1.493; Abbe's numbers ν: 50.56.

Example 3 (A1 Series) GDMA-MA

Dimethyl 3,3'-(((ethane-1,2-diylbis(oxy))bis(2-oxoethane-2,1-diyl)) bis(sulfanediyl))bis(2-methylpropanoate GDMA-MA

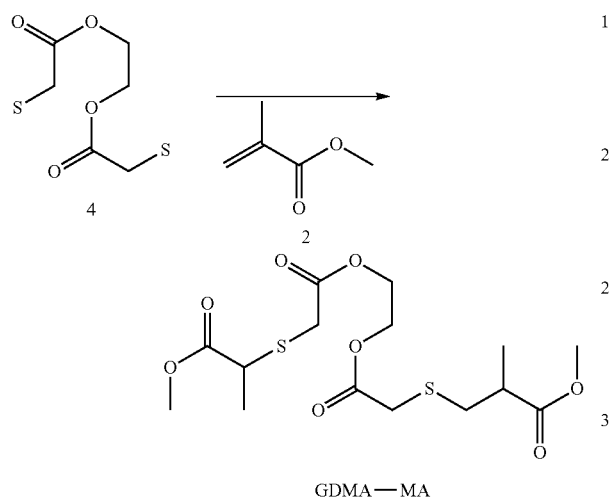

GDMA—MA 5 g (0.02 mol) dithiol 4 were reacted with 9.5 g (0.08 mol) methyl methacrylate 2 in a mixture of 10 mL THF and 10 mL DMA. 1.4 mL (0.01 mol) triethyl amine were added and the solution stirred for 72 h at room temperature. All volatile components were removed in vacuum, the residue was washed with aqueous 1 N HCl, extracted with DCM, washed several times with water, dried over MgSO$_4$, filtered and evaporated to give a colourless liquid (4.1 g, 41%).

NMR (400 MHZ, CDCl$_3$) δ=4.36 (s, 4H, CH$_2$CO, 3.70 (s, 6H, OCH$_3$), 3.26 (s, 4H, SCH$_2$CH), 2.98-2.92 (m, 2H, CH), 2.77-2.70 (m, 4H, OCH$_2$CH$_2$O).

n$_D$: 1.493; Abbe's numbers ν: 49.65.

Example 4 (A1 Series) DMPT-MA

Dimethyl 8-(((3-methoxy-2-methyl-3-oxopropyl)thio)methyl)-2,15-dimethyl-4,7,10,13-tetrathiahexadecanedioate DMPT-MA

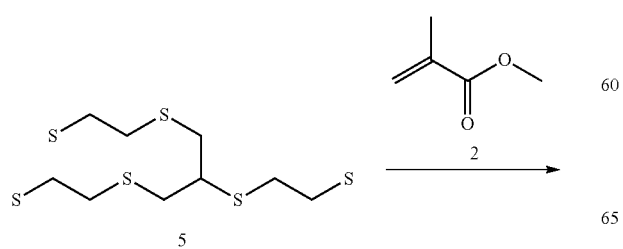

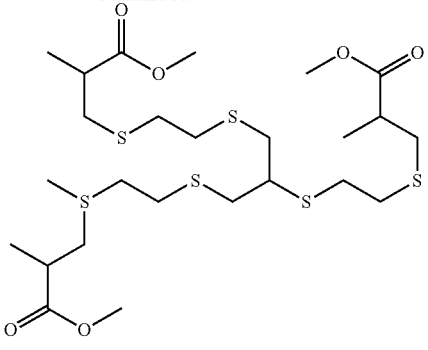

DMPT—MA 20 mL (0.2 mol) methyl methacrylate 2 and 3 mL (0.014 mol) trithiol 5 were mixed in 15 mL THF/DMF. 2.5 mL (0.014 mol) di-iso-propyl ethylamine were added and the obtained solution was stirred for 24 h at room temperature. All volatile components were removed in vacuum and 15 mL DMF was added and stirred for another 24 h. All volatile components were again removed in vacuum and the residue was purified by column chromatography [c-hexane/ethyl acetate (4:1)] to yield a pale yellow liquid (1.5 g, 20%).

NMR (400 MHZ, CDCl$_3$) δ=3.72 (s, 9H, OCH$_3$), 3.00-2.61 (m, 22H), 1.27-1.25 (d, 9H, CHCH$_3$).

n$_D$: 1.538; Abbe's numbers υ: 44.24

Example 5 (A1 Series) TMPMA-MA 2-ethyl-2-((2-mercaptoacetoxy)methyl)propane-1,3-diyl-bis (2-mercaptoacetate)-methyl-methacrylate (TMPMA-MA)

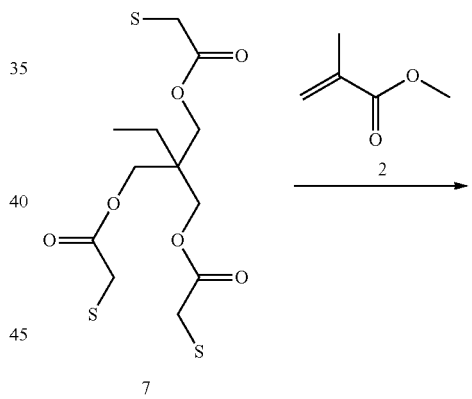

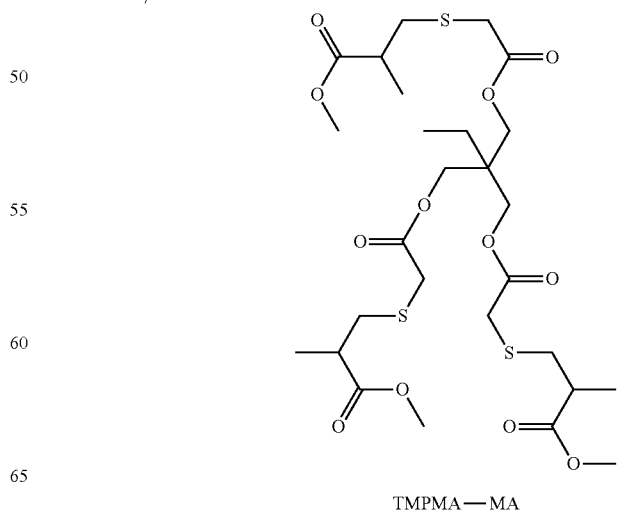

TMPMA—MA 30.0 g (0.084 mol) trimethylolpropan trimercaptoacetate 7 (TMPMA), 29.9 mL (0.27 mol) methyl methacrylate 2, 450 mL ethanol and 11.6 mL (0.084 mol) triethyl amine were stirred at room temperature for 2 h, thereafter an additional amount of 8.40 g triethyl amine was added. After stirring for 24 h at room temperature the solvent was evaporated and the residue was treated with aqueous 1N HCl and then extracted with dichloro methane. The organic phase was dried over MgSO$_4$, filtered and concentrated to give the product as pale yellow liquid. Highly pure material was obtained via silica gel chromatography [hexane/ethyl acetate (10:4)] and high vacuum treatment (80° C. for 10 h) to remove traces of solvent (42.8 g, 95%).

NMR (400 MHZ, CDCl$_3$) δ=4.09 (s, 6H, CCH$_2$O), 3.68 (s, 9H, COOCH$_3$), 3.23 (s, 6H, COCH$_2$S), 2.96-2.86 (st, 3H, SCH$_2$CHCH$_3$CO), 2.78-2.65 (m, 6H, SCH$_2$CHCH$_3$), 1.54-1.48 (q, 2H, CH$_3$CHC), 1.25-1.23 (d, 9H, CHCH$_3$), 0.92-0.88 (t, 3H, CH$_2$CH$_3$).

n$_D$: 1.502; Abbe's numbers ν: 49.60

Example 6 L (A2 Series) BSMD-$^t$BuMA

Di $^t$butyl-3'-(((1,4-dithiane-2,5-diyl)bis(methylene))bis(sulfanediyl))bis(2-methyipropanoate) BSMD-tBuMA

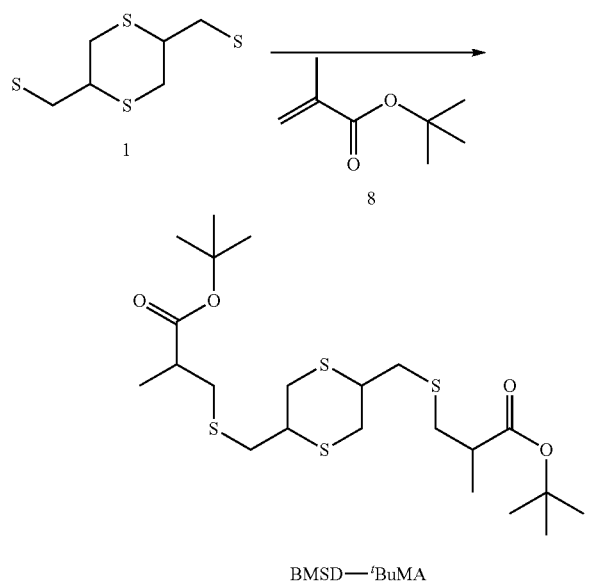

BMSD—$^t$BuMA

Dithiol 1 (5.0 g, 23.5 mmol) and t-butyl methacrylate 8 (13.4 g, 94.3 mmol) were dissolved in a mixture of 20 ml dimethylformamide and tetrahydrofuran (1:1 (vol:vol)) at room temperature. The reaction was started by the addition of 3.2 ml (23.5 mmol) triethyl amine. After three days at room temperature the mixture was evaporated in high vacuum and the residue was taken up in dichloro methane and successively extracted with 1N hydrogen chloride, water and brine. The organic phase was then filtered over MgSO$_4$ and removed in vacuum giving a yellow oil which was purified via silica gel chromatography [heptane/ethyl acetate (10:1)] yielding 7.2 g of a clear liquid which consisted of two isomers.

NMR (400 MHZ, CDCl$_3$) δ=1.2 (d, 6H), 1.48 (s, 18H), 2.5-3.5 (m, 16H).

n$_D$: 1.5227; Abbe's numbers ν: 44.26

Example 7 (A2 Series) BSMD-EtA

Diethyl-3'-(((1,4-dithiane-2,5-diyl)bis(methylene))bis(sulfanediyl))bis(2-methylpropanoate) BSMD-EtA

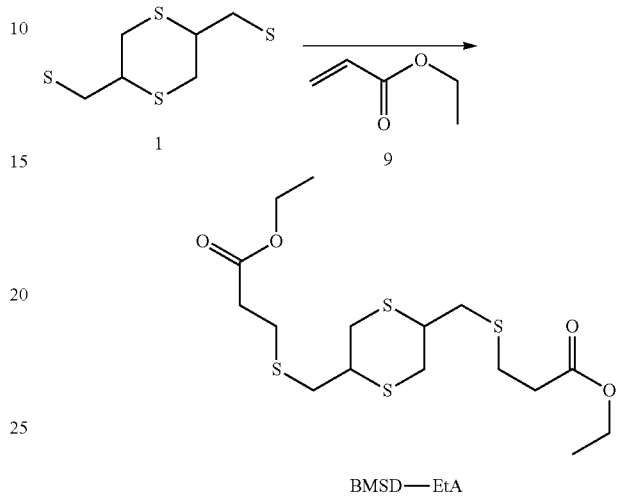

BMSD—EtA

Dithiol 1 (5.0 g, 23.5 mmol) and ethyl acrylate 9 (9.4 g, 94.2 mmol) were dissolved in a mixture of 20 ml dimethylformamide and tetrahydrofuran (1:1 (vol:vol)) at room temperature. The reaction was started by the addition of 3.2 ml (23.5 mmol) triethyl amine. After three days at room temperature the mixture was evaporated in high vacuum and the residue was taken up in dichloro methane and successively extracted with 1N hydrogen chloride, water and brine. The organic phase was then filtered over MgSO$_4$ and removed in vacuum giving a yellow oil which was purified via silica gel chromatography [heptane/ethyl acetate (3:1)] yielding 8.9 g of a clear liquid.

NMR (400 MHZ, CDCl$_3$) δ=1.3 (t, 6H), 1.48 (s, 18H), 2.6 (t, 4H), 2.65-3.4 (m, 14H), 4.2 (q, 4H).

n$_D$: 1.5505; Abbe's numbers υ: 43.26

Example 8 (A2 Series) BSMD-BnMA

Dibenzyl-3'-(((1,4-dithiane-2,5-diyl)bis(methylene))bis(sulfanediyl))bis(2-methylpropanoate) BSMD-BnMA

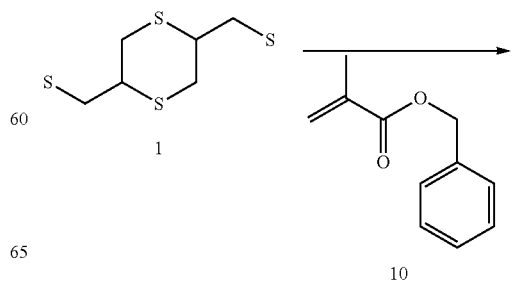

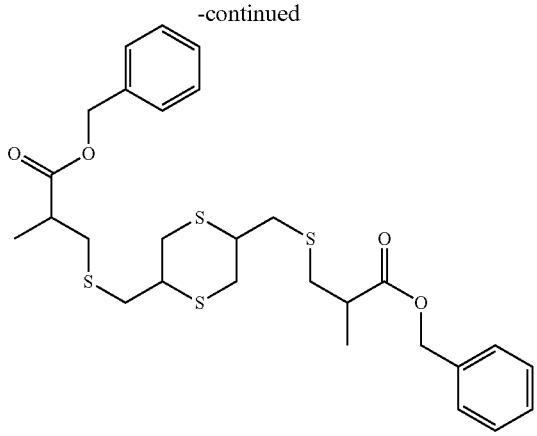

BMSD—BnMA

Dithiol 1 (5.0 g, 23.5 mmol) and benzyl methacrylate 10 (16.6 g, 94.2 mmol) were dissolved in a mixture of 20 ml dimethylformamide and tetrahydrofuran (1:1 (vol:vol)) at room temperature. The reaction was started by the addition of 3.2 ml (23.5 mmol) triethyl amine. After three days at room temperature the mixture was evaporated in high vacuum and the residue was taken up in dichloro methane and successively extracted with 1N hydrogen chloride, water and brine. The organic phase was then filtered over MgSO$_4$ and removed in vacuum giving a yellow oil which was purified via silica gel chromatography [heptane/ethyl acetate (5:1)] yielding 11.0 g of a clear liquid.

NMR (400 MHZ, CDCl$_3$) δ=1.3 (d, 6H), 2.5-3.4 (m, 16H), 2.6 (t, 4H), 5.2 (s, 4H), 7.33-7.42 (m, 10H).

n$_D$: 1.5819; Abbe's numbers u: 36.51

Example 9 (A2 Series) BSMD-$^i$BorA

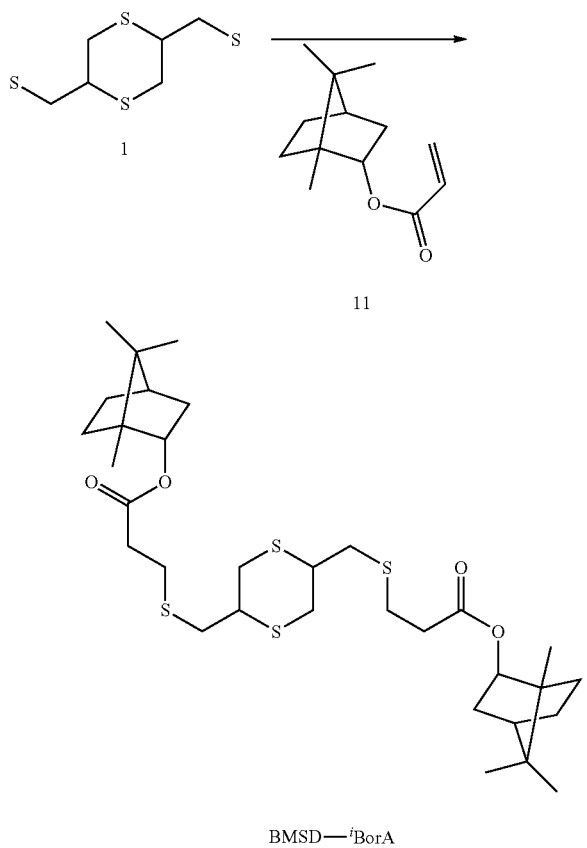

BMSD—$^i$BorA

Dithiol 1 (5.0 g, 23.5 mmol) and iso-bornyl acrylate 11 (19.6 g, 94.2 mmol) were dissolved in a mixture of 20 ml dimethylformamide and tetrahydrofuran (1:1 (vol:vol)) at room temperature. The reaction was started by the addition of (3.2 ml, 23.5 mmol) triethyl amine. After three days at room temperature the mixture was evaporated in high vacuum and the residue was taken up in dichloro methane and successively extracted with 1N hydrogen chloride, water and brine. The organic phase was then filtered over MgSO$_4$ and removed in vacuum giving a yellow oil which was purified via silica gel chromatography [heptane/ethyl acetate (10:1)] yielding 10.3 g of a very viscous clear liquid.

NMR (400 MHZ, CDCl$_3$) δ=0.95 (s, 12H), 1.0-1.3 (m, 6H), 1.45-1.55 (m, 2H), 1.6-1.85 (m, 8H), 2.5-2.6 (dd, 4H), 2.75-2.9 (m, 6H), 2.9-3.0 (m, 4H), 3.1-3.15 (d, 2H) 4.65 (m, 2H).

n$_D$: 1.5478; Abbe's numbers v: 46.84

Example 10 (A1 Series) TMPMA-tBuA

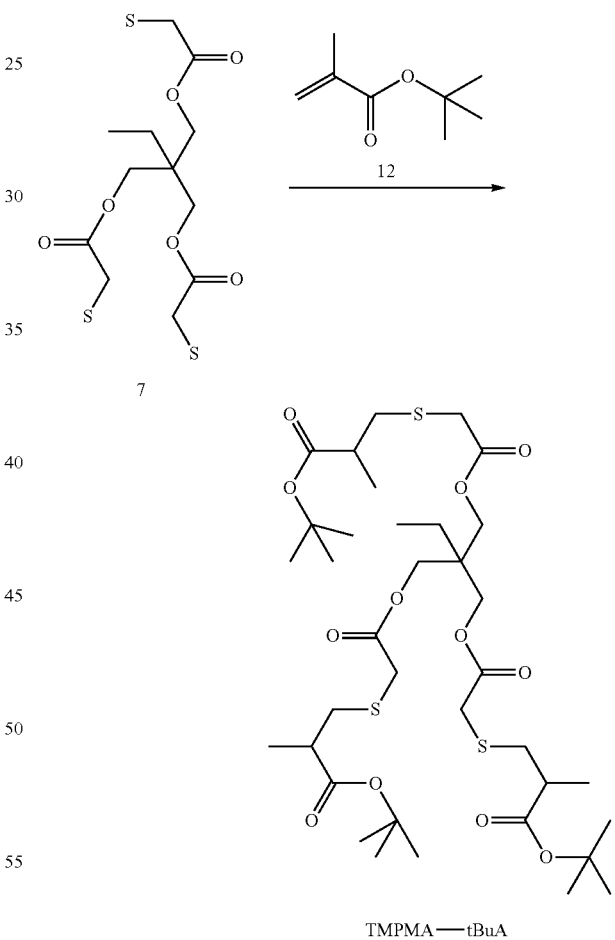

TMPMA—tBuA 20.0 g (0.056 mol) trimethylolpropan trimercaptoacetate 7 (TMPMA), 31.9 g (0.224 mol) $^t$butyl methacrylate 12, 250 mL ethanol and 5.7 mL (0.056 mol) triethyl amine were stirred at room temperature for 48 h. Thereafter the solvent was evaporated and a residue was obtained. Highly pure material was obtained via silica gel chromatography [dichloromethane/methanol (10:0.5)] and high vacuum treatment (80° C. for 10 h) to remove traces of solvent (29.4 g, 67%). NMR (400 MHZ, CDCl$_3$) δ=4.09 (s, 6H, CCH$_2$O), 3.24 (s, 6H, COCH$_2$S), 2.90-2.83 (dd, 3H, SCH$_2$C), 2.68-2.62 (dd, 2H, SCH$_2$C), 2.56 (m, 3H, CCHC), 1.53-1.47 (q, 2H, CH$_3$CH$_2$C), 1.43 (s, 27H, C(CH$_3$)$_3$), 1.20-1.18 (d, 9H, CHCH$_3$), 0.93-0.88 (t, 3H, CH$_2$CH$_3$).

$n_D$: 1.4838; Abbe's numbers v: 50.80

Example 11 (A1 Series) TMPMA-hydroxy EthylA

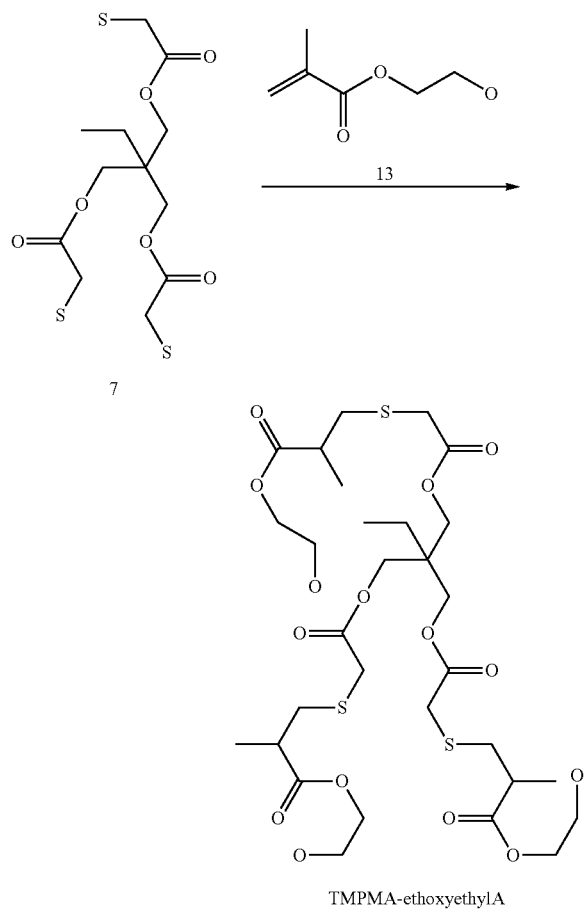

TMPMA-ethoxyethylA 10.0 g (0.028 mol) trimethylolpropan trimercaptoacetate 7 (TMPMA), 14.5 g (0.111 mol) 2-hydroxyethyl methacrylate 13, 150 mL ethanol and 2.8 g (0.028 mol) triethyl amine were stirred at room temperature for 24 h. Thereafter the solvent was evaporated and a residue was obtained. Highly pure material was obtained via silica gel chromatography [dichloromethane/methanol (10:0.6)] and high vacuum treatment (80° C. for 10 h) to remove traces of solvent (18.3 g, 88%).

NMR (400 MHZ, CDCl$_3$) δ=4.31-4.22 (m, 3H, (O)COCH$_2$), 4.19-4.14 (m, 3H, (O)COCH$_2$), 4.09 (s, 6H, CCH$_2$O), 3.84-3.80 (t, 6H, CH$_2$OH), 3.23 (s, 6H, COCH$_2$S), 2.96-2.89 (m, 3H, CCHC), 2.88-2.71 (m, 6H, SCH$_2$CH), 2.04 (s, 3H, OH), 1.55-1.49 (q, 2H, CH$_3$CH$_2$C), 1.20-1.18 (d, 9H, CHCH$_3$), 0.93-0.88 (t, 3H, CH$_2$CH$_3$).

$n_D$: 1.5111; Abbe's numbers v: 50.30

Example 12 (A1 Series) TMPMA-2 hydroxymethyl ethylA

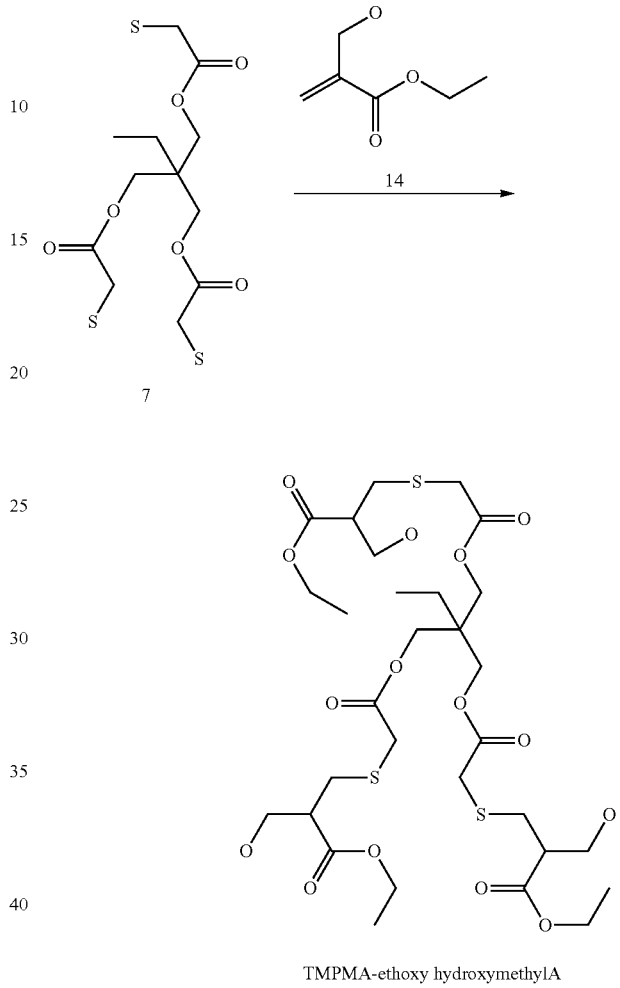

TMPMA-ethoxy hydroxymethylA 7.6 g (0.021 mol) trimethylolpropan trimercaptoacetate 7 (TMPMA), 10.0 g (0.077 mol) 2-hydroxymethyl ethylacrylate 14, 100 mL ethanol and 2.2 g (0.022 mol) triethyl amine were stirred at room temperature for 48 h. The mixture has then been taken up in ethylacetate and subsequently been extracted with 1 N HCl, water and brined and stored over sodium sulfate and then filtered. Thereafter the solvent was evaporated and a residue was obtained. Highly pure material was obtained via silica gel chromatography [dichloromethane/methanol (50:1.0)] and high vacuum treatment (80° C. for 10 h) to remove traces of solvent (7.1 g, 45%).

NMR (400 MHZ, CDCl$_3$) δ=4.23-4.18 (q, 6H, (O)COCH$_2$CH$_3$), 4.14 (s, 6H, CCH$_2$O), 3.89-3.85 (d, 6H, CH$_2$OH), 3.30 (s, 6H, COCH$_2$S), 3.02-2.93 (m, 6H, SCH$_2$CH), 2.84-2.78 (m, 6H, OH, CCHC), 1.57-1.51 (q, 2H, CH$_3$CH$_2$C), 1.31-1.28 (t, 9H, OCH$_2$CH$_3$), 0.95-0.91 (t, 3H, CH$_2$CH$_3$).

$n_D$: 1.5100; Abbe's numbers v: 50.40

Example 13 (A1 Series) 2 ethyl, 2-(2thio-methylmethyacrylate) 1,3 di(thiomethylmethacrylate) ETT

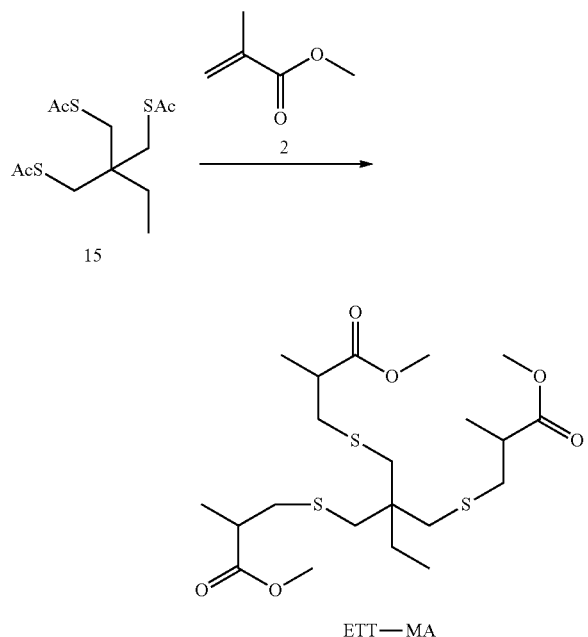

13.25 g (0.043 mol) of triacetate 15 are dissolved at room temperature in a mixture of 70 ml methanol containing 351 mg of sodium methanolate and 15.5 g (0.155 mol) methyl methacrylate 2 and stirred for 24 h. The mixture is evaporated, the resulting residue dissolved in diethylether and filtered over char coal. Evaporation gives an oil which is purified by silica gel chromatography [hexane/ethylacetate (10:2)] and high vacuum treatment (80° C. for 10 h) to remove traces of solvent (18.3 g, 88%).

NMR (400 MHZ, CDCl$_3$) δ=3.66 (s, 9H, CH$_3$O), 2.84-2.70 (m, 3H, SCH), 2.70-2.65 (m, 3H, SCH), 2.64-2.54 (m, 9H, CH$_2$S, CCHC), 1.41-1.35 (q, 2H, CH$_3$CH$_2$C), 1.22-1.20 (d, 9H, CCH$_3$), 0.81-0.77 (t, 3H, CH$_2$CH$_3$).

n$_D$: 1.5088; Abbe's numbers ν: 48.40

Example 14 (A1 Series) 2 ethyl, 2-(2thio-$^t$butylm-ethyacrylate) 1,3 di(thio$^t$butylmethacrylate) ETT

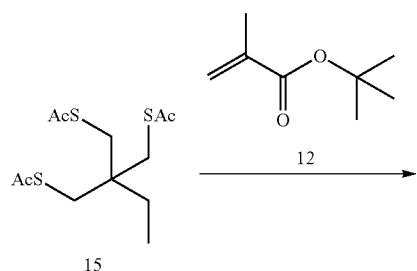

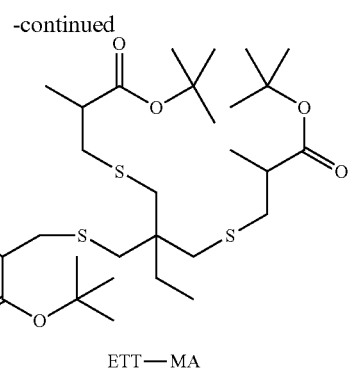

4.50 g (0.014 mol) of triacetate 15 are dissolved at room temperature in a mixture of 25 ml methanol containing 110 mg of sodium methanolate and 8.3 g (0.058 mol) $^t$butyl methacrylate and stirred for 48 h. The mixture is evaporated, the resulting residue dissolved in dichloromethane and subsequently extracted with 1 N HCl, water and brine, filtered over sodium sulfate and evaporated. The oily residue is purified by silica gel chromatography [hexane/ethylacetate (10:0.5)] and high vacuum treatment (80° C. for 10 h) to remove traces of solvent (7.2 g, 82%).

NMR (400 MHZ, CDCl$_3$) δ=2.83-2.78 (dd, 3H, SCH), 2.63 (s, 6H, SCH$_2$), 2.59-2.52 (m, 6H, CH$_2$S, CCHC), 1.45-1.42 (m, 29H, CH$_3$CH$_2$C, CCH$_3$), 0.88-0.81 (t, 3H, CH$_2$CH$_3$).

n$_D$: 1.4842; Abbe's numbers ν: 50.20.

The invention claimed is:
1. An optical lense comprising:
    a liquid thioether carboxylic acid ester, wherein the thioether carboxylic acid ester is a reaction product of
    A) a compound of the formula
        a) (A1)

wherein R$_1$ is hydrogen, linear or branched C$_1$-C$_7$ alkyl; R$_2$ is hydrogen or a linear or branched C$_1$-C$_8$-alkyl containing at least one sulfhydryl moiety (SH); R$_3$ and R$_4$ are independently selected from a linear or branched C$_1$-C$_8$-alkyl containing at least one sulfhydryl moiety (SH), and optionally one or two CH$_2$ group(s) of R$_2$ and/or R$_3$ and/or R$_4$ is/are replaced by O, S and/or C=O and
    B) a compound of the formula (B)

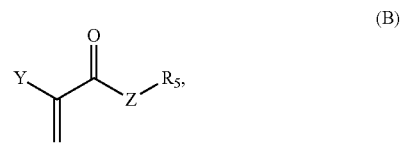

wherein Y is hydrogen or methyl; Z is O; R$_5$ is a linear or branched saturated C$_1$-C$_8$ alkyl or a saturated bicyclic aliphatic system selected from the group consisting of norbomyl-, isonorbornyl-, pinenyl-, menthyl-, camphyl- or an aryl system selected from phenyl and benzyl.

2. The optical lense according to claim 1, wherein in the formula (A1) $R_1$ is hydrogen or ethyl; $R_2$ is hydrogen or a linear $C_1$-$C_6$-alkyl containing at least one sulfhydryl moiety (SH); $R_3$ and $R_4$ are independently selected from a linear $C_2$-$C_6$-alkyl containing at least one sulfhydryl moiety (SH), and one or two $CH_2$ group(s) of $R_2$ and/or $R_3$ and/or $R_4$ is/are replaced by O, S and/or C=O.

3. The optical lense according to claim 1, wherein in the formula (A1) $R_1$ is hydrogen; $R_2$ is a linear $C_1$-$C_5$-alkyl containing at least one sulfhydryl moiety (SH); $R_3$ and $R_4$ are independently selected from a linear $C_3$-$C_5$-alkyl containing at least one sulfhydryl moiety (SH), and one $CH_2$ group of $R_2$ and/or $R_3$ and $R_4$ is replaced by S.

4. The optical lense according to claim 1, wherein in the formula (A1) $R_1$ is hydrogen or ethyl; $R_2$ is hydrogen or a linear $C_3$-$C_5$-alkyl containing at least one sulfhydryl moiety (SH); $R_3$ and $R_4$ are independently selected from a linear $C_3$-$C_5$-alkyl containing at least one sulfhydryl moiety (SH), and two $CH_2$ groups of $R_2$ and/or $R_3$ and $R_4$ are replaced by O and C=O.

5. The optical lense according to claim 4, wherein two $CH_2$ groups of $R_2$ and/or $R_3$ and $R_4$ are replaced by O and C=O, and O and C=O are directly linked.

6. The optical lense according to claim 1, wherein Y is hydrogen or methyl; Z is O; $R_5$ is linear saturated $C_1$-$C_3$ alkyl.

7. The optical lense according to claim 1, wherein Y is hydrogen or methyl; Z is O; $R_5$ is a linear or branched saturated $C_1$-$C_4$ alkyl or a saturated bicyclic aliphatic system selected from the group consisting of norbornyl-, isonorbornyl-, pinenyl-menthyl-, camphyl- or an aryl system selected from phenyl and benzyl.

8. The optical lense according to claim 1, wherein the reaction product is obtained by a 1,4-addition mechanism of the at least one sulfhydryl group of the compound of the formula (A1) and the compound of the formula (B).

9. The optical lense according to claim 1, wherein the reaction product is of the general formula (C1)

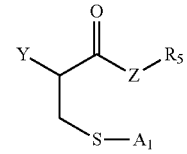

C1 wherein Y, Z, and $R_5$ are as defined in claim 1 and wherein $A_1$ is (A1) as defined in claim 1.

10. The optical lense according to claim 1, wherein the thioether carboxylic acid ester has a refractive index of 1.27-1.9, and/or an Abbe's number of 35-110.

* * * * *